United States Patent
Creasman et al.

(10) Patent No.: US 8,182,266 B2
(45) Date of Patent: May 22, 2012

(54) DENTAL TOOL

(76) Inventors: Susan M. Creasman, Andrews, NC (US); Deborah E. Creasman, Delray Beach, FL (US)

( * ) Notice: Subject to any disclaimer, the term of this patent is extended or adjusted under 35 U.S.C. 154(b) by 207 days.

(21) Appl. No.: 12/460,713

(22) Filed: Jul. 23, 2009

(65) Prior Publication Data

US 2009/0286199 A1 Nov. 19, 2009

Related U.S. Application Data

(63) Continuation-in-part of application No. 11/713,259, filed on Mar. 2, 2007, now abandoned.

(60) Provisional application No. 60/875,904, filed on Dec. 20, 2006.

(51) Int. Cl.
*A61C 3/00* (2006.01)
*B25B 27/00* (2006.01)
*B25B 27/14* (2006.01)

(52) U.S. Cl. ............. 433/141; 433/3; 433/147; 29/270; 29/278

(58) Field of Classification Search ............. 433/2, 3, 433/4, 5, 141–148, 159–160; 294/10, 24, 294/26; 7/151, 152; 206/368; 29/270, 278; 254/25, 21; 30/2, 406, 408, 410; 606/160–162; 269/3, 6; 81/3.55

See application file for complete search history.

(56) References Cited

U.S. PATENT DOCUMENTS

| | | | |
|---|---|---|---|
| 840,580 A * | 1/1907 | MoMillian | 7/144 |
| 2,057,077 A | 10/1936 | Zimmer | |
| 2,602,998 A * | 7/1952 | Sprague | 433/141 |
| 3,690,005 A | 9/1972 | Edelman | |
| 3,702,028 A | 11/1972 | Edelman | |
| 3,842,696 A * | 10/1974 | Wayne | 81/424.5 |
| 3,898,738 A * | 8/1975 | Linder | 433/159 |
| 4,274,826 A | 6/1981 | Huey et al. | |
| 4,474,500 A | 10/1984 | Lynch | |
| 4,580,302 A * | 4/1986 | Barth | 7/152 |
| 4,627,817 A | 12/1986 | Higa | |
| 4,657,510 A | 4/1987 | Gittleman | |
| 4,723,540 A * | 2/1988 | Gilmer, Jr. | 606/75 |
| 4,907,965 A | 3/1990 | Martin | |
| 4,931,016 A | 6/1990 | Sillard | |
| 5,026,285 A | 6/1991 | Durr et al. | |
| 5,133,662 A | 7/1992 | Metcalfe | |

(Continued)

FOREIGN PATENT DOCUMENTS

CA 1 227 677 10/1987

(Continued)

*Primary Examiner* — Todd Manahan
*Assistant Examiner* — Yogesh Patel
(74) *Attorney, Agent, or Firm* — Malloy & Malloy, P.L.

(57) ABSTRACT

A dental tool for the removal of dental appliances or oral devices from a user's mouth comprises a universal handle which is substantially cylindrical. Interconnected thereto is an engagement head comprising a first engagement member extending upward and outward opposite the handle, and a second engagement member extending downward and outward opposite the handle. The first engagement member and second engagement member are disposed in angled relation to one another, each terminating in a broad distal tip having a curvilinear edge. The first and second engagement members further contain contact surfaces for contacting and engaging the dental appliance or oral device. The dental tool is comprised of a rigid material, with a resilient portion overlaid on at least the contact surfaces of the first and second engagement members and distal tips thereof. The dental tool may also be stored in a case to make a kit for removing oral devices.

5 Claims, 7 Drawing Sheets

U.S. PATENT DOCUMENTS

| | | | |
|---|---|---|---|
| 5,217,371 A | 6/1993 | Lukase et al. | |
| 5,378,151 A | 1/1995 | Lukase et al. | |
| 6,139,321 A | 10/2000 | MacCulloch | |
| 6,206,696 B1 | 3/2001 | Day | |
| 6,247,933 B1 | 6/2001 | Wagner et al. | |
| 6,287,115 B1 | 9/2001 | Lustig et al. | |
| 6,311,580 B1 * | 11/2001 | Nagy | 81/3.55 |
| 6,352,291 B1 * | 3/2002 | Tortajada | 294/24 |
| 6,474,988 B1 * | 11/2002 | Georgakis et al. | 433/4 |
| 6,796,797 B2 | 9/2004 | Muller et al. | |
| 6,951,462 B2 | 10/2005 | Kumar et al. | |
| 7,011,517 B2 | 3/2006 | Nicozisis | |
| 7,059,850 B1 | 6/2006 | Phan et al. | |
| 2003/0099918 A1 | 5/2003 | De Luca | |
| 2006/0131906 A1 | 6/2006 | Maurer et al. | |

FOREIGN PATENT DOCUMENTS

| | | |
|---|---|---|
| CA | 1 234 302 | 3/1988 |
| CA | 2038327 | 9/1992 |
| CA | 1319035 | 6/1993 |
| CA | 1321907 | 9/1993 |
| CA | 2182858 | 8/1995 |
| CA | 2274883 | 6/1998 |
| CA | 2 351 420 | 6/2000 |
| CA | 2345679 | 2/2001 |
| CA | 2 398 885 | 8/2001 |
| CA | 2 511 785 | 7/2004 |
| WO | WO 98/29053 | 7/1998 |

* cited by examiner

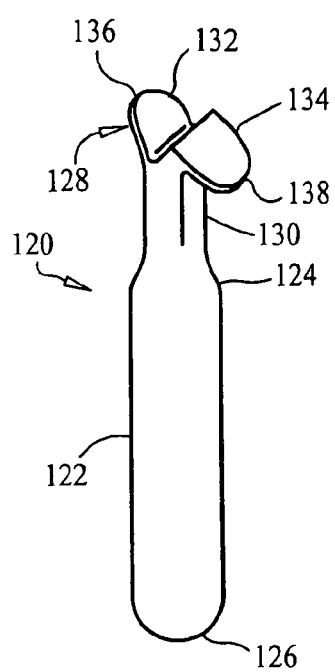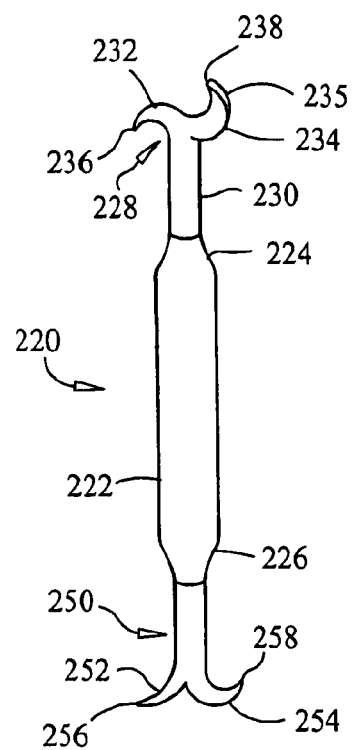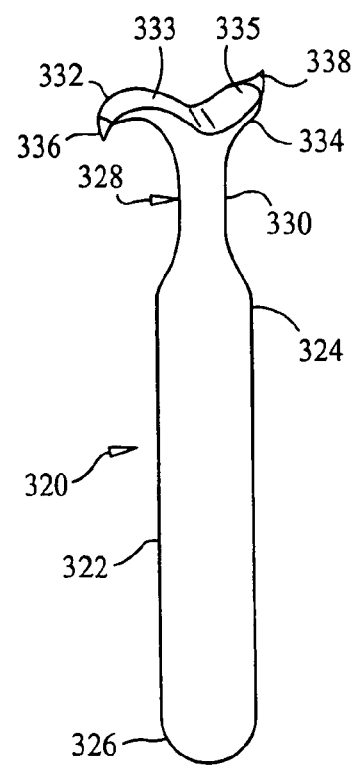
FIG. 1　　　FIG. 2　　　FIG. 3
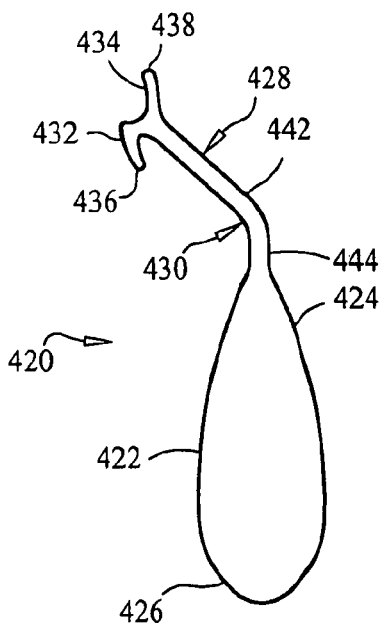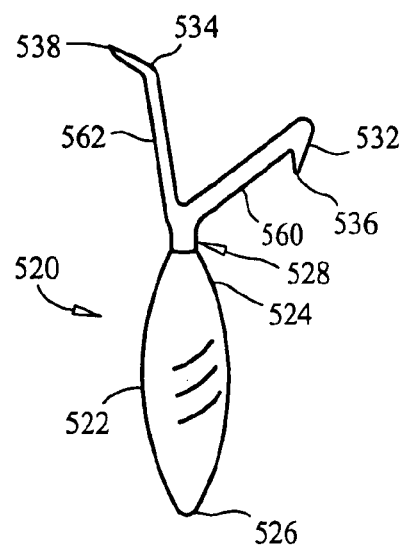
FIG. 4　　　FIG. 5

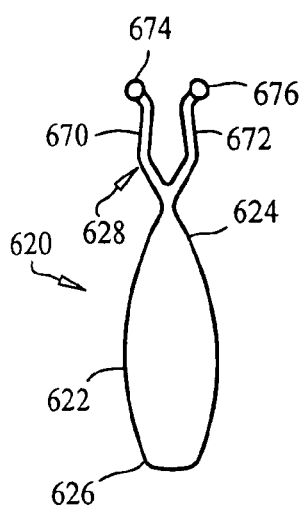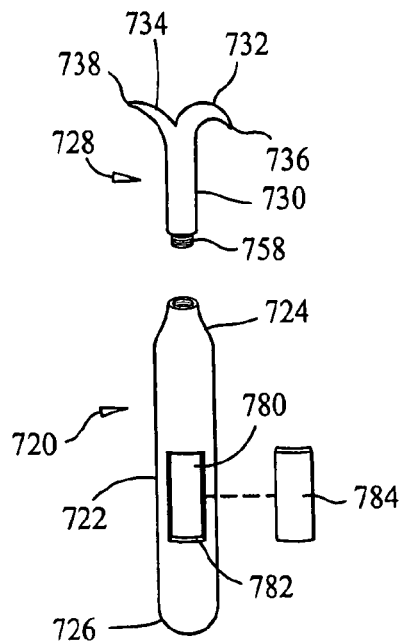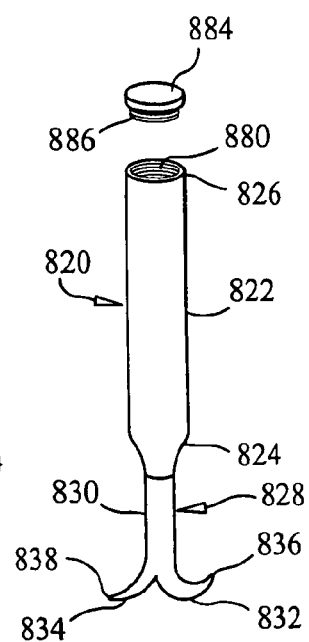
FIG. 6  FIG. 7  FIG. 8
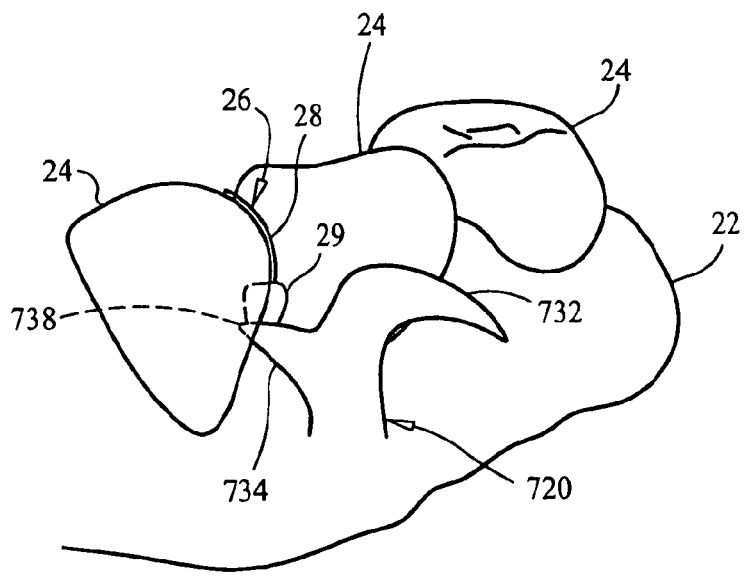
FIG. 9

DENTAL TOOL

CLAIMS OF PRIORITY

The present application is a continuation-in-part of previously filed and currently U.S. patent application Ser. No. 11/713,259 filed Mar. 2, 2007, now abandoned which claims the benefit of U.S. Provisional Patent Application Ser. No. 60/875,904 filed Dec. 20, 2006, both of which are incorporated herein by reference in their entirety.

FIELD OF THE INVENTION

The present invention relates to dental instruments in general and more particularly to dental instruments to aid in the removal of dental appliances and oral devices.

BACKGROUND OF THE INVENTION

Dental hygiene and tooth maintenance is a very important part of everyday life. Healthy teeth are not only aesthetically pleasing, but are also a necessary and vital part of our daily routine of food consumption. A full set of teeth allow us to chew our food to aid in the digestive process, thus we place a high emphasis on dental care to retain as many of our natural teeth as possible. However, over the centuries, humans have been contending with the loss of some or all of their teeth as a result of accidents, injuries, or oral disease, and the loss of teeth remains a problem to this day in spite of the advances of modern dental medicine. Since the human body does not naturally replace missing teeth, dental prosthetics have been developed to provide artificial teeth.

Dental prosthetics, also known as dental appliances, have been utilized for centuries, starting with crude ill fitting dentures made of wood or bone. These initial attempts at dental prosthetics, while an improvement over having no teeth, suffered from the problem of retention, or more specifically, how well the denture is prevented from moving in the vertical plane in the opposite direction of insertion. Initially, retention of mandibular (lower) dentures and more particularly maxillary (upper) dentures relied on conforming the interior surface of the denture to closely mimic the topographical contours of the portion of the mouth in which the dentures were to be retained. For the dentures that relied solely on matching the contour of the mouth and more specifically the mucosa that underlies the dentures, retention relied on the forces of surface tension, suction, plain old friction, and even adhesives to keep the dentures from becoming dislodged. Dentures that relied solely on these forces, while greatly restoring aesthetics, restored only a small portion of the person's original tooth function for biting and chewing. Further, after a person has used dentures for a time period, the underlying bone in the person's jaw, and more specifically the alveolar bone in which the teeth normally reside, has tended to shrink and atrophy thereby causing well fitting dentures to now become ill fitting dentures with an undesirable decrease in retention.

Full dentures are only a part of the dental prosthetic universe. Other forms of dental prosthetics include partial dentures and fixed and removable bridges. Fixed bridges are permanently affixed to neighboring teeth and do not need to be removed on a regular basis. However, full dentures, partial dentures, and removable bridges do need to be removed on a regular basis for cleaning and for personal hygienic reasons. Food particles can become lodged in the areas between a person's natural teeth and the prosthetic or even between the mucosa and the prosthetic. Some partials and removable bridges can be held in place with stainless steel wires that are closely formed to the interior surfaces of adjoining teeth and are then anchored to the teeth utilizing a clasp formed with the wire such as a ball clasp which engages an undercut formed by two adjacent teeth.

As the practice of dental prosthetics has progressed over the years through scientific discovery, experimentation and innovation, researchers have made some important discoveries. One of the discoveries is that the forces of biting and chewing which are normally transferred by the teeth to the alveolar bone is the mechanism by which the alveolar bone is maintained in good health, and that the absence of those directly transferred forces is what causes the atrophying of the bone. Thus, implants have now become an accepted practice for introducing dental prosthetics to replace missing teeth. An implant is usually a post that is embedded in the alveolar bone, and after a healing period the dental prosthetic is attached to it. A single implant can be utilized to support one missing tooth, or two or more implants can support a partial denture, removable bridge, or even a full denture. The implants greatly improve the retention factor by the inclusion of a clasping mechanism between the post/implant and the prosthetic device.

In addition to dental prosthetics, there are a wide range of dental and oral appliances that are frequently used to enhance dental aesthetics and protection which also require strong retention and safe removal. For instance, orthodontic advances have produced retainers and products to adjust the placement of teeth such as INVISALIGN® that must tightly fit the user's teeth, and yet also must be removable. Cosmetic appliances such as bleaching trays which are used in the tooth whitening process must fit the teeth well enough to keep the whitening agents in contact with the teeth and yet be removable once treatment is complete. Other cosmetic appliances such as SNAP-ON SMILE® and ANGELLIFT® must also fit tightly in the mouth of a user in order to provide the desired aesthetic appearance. Dental protection appliances such as sports mouth guards for use by athletes, and night guards and bite splints which are used to prevent grinding away of tooth enamel during sleep, are molded to fit the teeth of the user and yet must be removable. Even oral appliances used in treating disorders such as sleep apnea, snoring, and tempromandibular joint (TMJ) disorder must also fit the teeth tightly in order to remain in place and be effective and yet still must be removable.

Advances in technology have yielded new dental and oral products, as well as new methods of creating these products. These new methods have led to the development of more accurately fitting dental appliances and oral products, with increased retention over their predecessors. Concurrent with these advances in oral device retention are the problems of removal for those devices that are meant to be removed on a regular basis for cleaning and oral hygiene. Whether the retention is that of suction, surface tension and adhesive forces on an upper maxillary denture or the forces required to overcome the mechanical clasping of a partial denture on implants, the increased retention forces of today's prosthetics and oral devices also increases the removal forces required to dislodge them. Often the wearer's options for removal of the device are grasping the device and pulling, or alternatively, attempting to hook a fingernail on an edge of the device and applying force to dislodge the device. Neither of these methods is desirable, since grasping forces on the device are often countered by the presence of saliva or other viscous compounds on the device. Likewise, attempting to hook a fingernail behind a feature of the device can cause injury to the underlying mucosa with the risk of infection and prolonged discomfort until the injured tissue heals. This problem is particularly acute among the elderly, frail and disabled who are also the ones most likely to use dental prosthetics and appliances. The difficulty of removal often results in these users leaving the appliances or devices in and thus forgoing the cleaning and oral hygiene required for good dental health.

Thus what is desired is a dental instrument to aid in the removal of dental prosthetics and oral devices to overcome the retention forces of the dental device whether by suction, implants, or wire clasps.

SUMMARY OF THE INVENTION

The present invention is directed to a hand held dental tool that satisfies the need to overcome dental prosthetic and oral device retention forces to easily and safely remove the prosthetic or device. The hand held dental tool comprises a handle that facilitates a sturdy grip and an engagement head affixed an end of the handle for engaging the prosthesis or device. The engagement head has dual fingers extending oppositely away from the head wherein a first finger extends upwardly from the head and a second finger extends downwardly from the head for engaging lower and upper prostheses or devices, respectively.

Another aspect of the present invention is a hand held dental tool for removing dental prostheses and oral appliances from a user's mouth wherein the dental tool has a shaft like handle having first and second ends with a neck extending from the first end. A first dual fingered head is formed at an end of the neck opposite from the handle with a first finger extending downwardly from the head and an opposing second finger extending upwardly from the head. The fingers can employ different shapes to facilitate dislodging of the prosthesis or appliance from the user's mouth.

Another aspect of the present invention is a hand held dental tool for removing dental prostheses and oral appliances from a user's mouth that includes a handle and a head for engaging a dental appliance to be removed. The head further has a first arm and second arm wherein each arm extends away from the handle and each said arm has a suction cup affixed to a free end thereof. The suction cups are laterally separated one from the other and are substantially coplanar.

Yet another aspect of the present invention is a hand held dental tool for removing dental prostheses and oral devices wherein the dental tool has a substantially cylindrical and universal handle interconnected to an engagement head. A first engagement member is structured to extend upwardly and outwardly from the engagement head, and a second engagement member is structured to extend outwardly and downwardly from the engagement head. The first and second engagement members are configured in angled relation to one another, and each terminates in a distal tip. The universal handle is structured to enable the operative positioning of the distal end of the first or second engagement member perpendicular to any part of the dental prosthesis or oral device within the mouth of a user.

Still another aspect of the present invention is a dental tool for removal of dental prostheses and oral devices wherein the dental tool has a handle and at least first and second engagement members. The first and second engagement members further include contact surfaces for contacting and engaging the dental prosthesis or oral device in order to facilitate removal of the same. The dental tool is composed of a rigid material, with resilient material overlain on at least the contact surfaces of the first and second engagement heads to further facilitate engagement with and removal of the dental prosthesis or oral device.

Another aspect of the present invention is a kit for the removal of an oral device comprising a dental tool having a handle and at least two engagement members, and a case for storage of the dental tool when not in use.

These and other features, aspects, and advantages of the invention will be further understood and appreciated by those skilled in the art by reference to the following written specification, claims and appended drawings.

BRIEF DESCRIPTION OF THE DRAWINGS

For a fuller understanding of the nature of the present invention, reference should be made to the following detailed description taken in conjunction with the accompanying drawings in which:

FIG. 1 is an elevation view of a dental tool embodying the present invention including an upwardly extending finger and a downwardly extending finger;

FIG. 2 is an elevation view of a dental tool embodying the present invention wherein an alternate engagement head embodiment is affixed to both ends of a handle;

FIG. 3 is an elevation view of a dental tool embodying the present invention including an alternate embodiment of an engagement head;

FIG. 4 is an elevation view of a dental tool embodying the present invention and having an alternate embodiment engagement head with an angled neck;

FIG. 5 is an elevation view of a dental tool embodying the present invention and having an alternate embodiment engagement head with a bifurcated neck and one finger at the end of each arm of the neck;

FIG. 6 is an elevation view of an alternate embodiment of the dental tool wherein the head includes a bifurcated neck with a suction cup affixed to the ends of each arm of the bifurcated neck;

FIG. 7 is an elevation view of a dental tool embodying the present invention wherein the engagement head is removable from a handle having a hollow interior and the handle includes a removable panel for access to the interior;

FIG. 8 is a reverse elevation view of a dental tool embodying the present invention and similar to the tool of FIG. 7 wherein access to the handle interior is obtained through a removable cap at the end of the handle;

FIG. 9 is a perspective view of a dental tool as embodied by FIG. 7 wherein one of the fingers is dislodging a ball clasp of a dental appliance;

Like reference numerals refer to like parts throughout the several views of the drawings.

DETAILED DESCRIPTION OF THE PREFERRED EMBODIMENT

Figure 10:
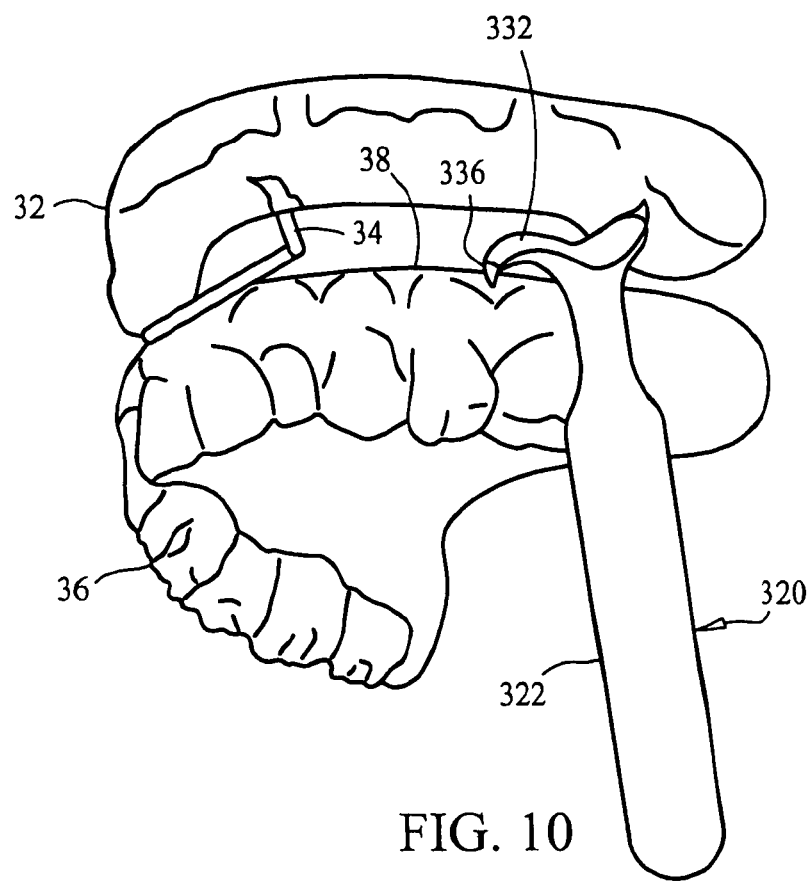
FIG. 10 is a perspective view of the dental tool as embodied by FIG. 3 dislodging a full maxillary denture from a user's mouth.

For purposes of description herein, the terms "upper", "lower", "left", "rear", "right", "front", "vertical", "horizontal", and derivatives thereof shall relate to the invention as oriented in FIGS. 1 and 10. However, one will understand that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Turning to the drawings, FIG. 1 shows a dental tool 120 which is one of the preferred embodiments of the present invention and illustrates its various components. Dental tool 120 has a shaft-like handle 122 which has a first end 124 and a second end 126. An engagement head 128 includes a neck 130 that is affixed to first end 124 of handle 122. Dual fingers 132 and 134 extend from an end of neck 130 opposite from handle 122. First finger 132 extends from head 128 in a generally upward manner for engaging a mandibular or lower dental prosthesis, and second finger 134 extends from engagement head 128 in a generally downward manner, and oppositely from finger 132, for engaging a maxillary or upper dental prosthesis. Both fingers 132 and 134 have a straight or linear configuration with rounded tips 136 and 138 respectively to prevent injury to the user's mucosa underlying the dental prosthetic.

FIGS. 2-8 illustrate alternate embodiments of dental tool 120 wherein alternately configured features thereof that correspond in description and function to those features of dental tool 120 will have reference numerals that have the same last two numerals while the preceding numeral will correspond to the figure number of the embodiment.

As illustrated in FIG. 2, an alternate embodiment dental tool 220 includes a handle 222 having first and second ends 224, 226 wherein a first engagement head 228 is affixed to first end 224 and a second engagement head 250 is affixed to second end 226. First engagement head 228 includes a neck 230 with first and second fingers 232 and 234 extending oppositely therefrom wherein first finger 232 extends substantially horizontally therefrom in a downwardly arcuate convex manner terminating at tip 236, and second finger 234 extends substantially vertically therefrom in an upwardly arcuate concave manner terminating at tip 238. As illustrated, finger 234 can also have an outer surface 235 that is generally shaped like a human fingernail. Second engagement head 250 affixed to second end 226 of handle 222 includes fingers 252 and 254 extending therefrom. Each of fingers 252 and 254 has a generally circular cross-section that extends from head 250 in an arcuately convex manner wherein the arcuate radius of second finger 254 is smaller than the arcuate radius of first finger 252 and further wherein first tip 256 extends in a direction away from handle 222 and second tip 258 extends in a direction toward handle 222.

FIG. 3 illustrates alternate embodiment 320 wherein handle 322 includes first and second ends 324 and 326 with an engagement head 328 including a neck 330 affixed to first end 324. First finger 332 extends from engagement head 328 in a generally horizontal and downwardly convex manner. In like manner, second finger 334 oppositely extends from head 320 in a generally horizontal and upwardly concave manner. First and second fingers 332 and 334 are substantially rigid and terminate with resilient tips 336 and 338 affixed thereto, respectively. Further, first and second fingers 332 and 334 can also have generally convex upper surfaces 333 and 335 to provide a generally fingernail shaped configuration.

Turning to FIG. 4, dental tool embodiment 420 has an ergonomically teardrop shaped handle 422 having a first small end 424 to which engagement head 428 is affixed and a large second end 426 that more comfortably fits within the grasp of a user than a handle having a cylindrical configuration. Neck 430 of engagement head 428 has two segments 442 and 444 that are angularly arranged one with respect to the other. The angular arrangement of neck segments 442 and 444 facilitates a user holding handle 422 in a more comfortable position while simultaneously permitting fingers 432 and 434 to engage a dental prosthesis or oral device at an optimal angle. Downwardly extending finger 436 and upwardly extending finger 434 can be generally circular in cross-section and terminate at tips 436 and 438 that are generally spherically configured to prevent injury to the mucosal layer underlying the dental prosthesis to be removed with dental tool 420.

Dental tool embodiment 520 as shown in FIG. 5 has a handle 522 with an alternate ergonomic configuration having ends 524 and 526 wherein engagement head 528 is affixed to handle end 524. Engagement head 528 has a bifurcated neck comprising first and second arms 560 and 562 arranged at an angle one to the other. First arm 560 includes first downwardly extending finger 532 terminating at tip 536 for engaging an upper dental prosthesis to be removed. In like manner, second arm 562 includes second upwardly extending finger 534 terminating at tip 538 for engaging a lower dental prosthesis to be removed.

Turning to FIG. 6, an alternate embodiment dental tool 620 is illustrated with an ergonomic handle having ends 624 and 626 wherein an engagement head 628 is affixed to end 624. Engagement head 628 includes spaced apart arms 670 and 672 wherein arms 670 and 672 terminate with resilient suction cups 674 and 676 respectively for engaging a dental prosthesis or oral device. The suction cups 674 and 676 are diametrically sized to engage a continuous smooth surface of the prosthesis to be removed and to provide sufficient disengagement force to the prosthesis without disengaging from the continuous surface of the prosthesis to which the cups 674 and 676 are engaged.

FIG. 7 shows a dental tool embodiment 720 wherein handle 722 is formed such that it defines an internal void 780 that is accessible through aperture 782 which receives a removable panel 784. In this manner, handle 722 can be utilized for storage. Additionally, engagement head 728 can be removable from handle 722. Engagement head 728 has an engagement feature 758 such as threads or a snap-in retaining feature known in the art at an end of neck 730 which is received in end 724 of handle 722. Engagement head 728, like those previously described, includes an upwardly extending finger 734 terminating at tip 738 and a downwardly extending finger 732 terminating at tip 736.

FIG. 8 illustrates an alternate embodiment dental tool 820 similar to dental tool 720 wherein handle 822 defines an internal void 880 which is accessible by removable end cap 884 at handle end 826. End cap 884 includes an engagement feature 886 such as threads or a snap-in retaining feature known in the art. Dental tool 820 includes engagement head 830 extending from handle end 824 and can, like the embodiment of dental tool 720, be removable. Engagement head 828, also like those previously, includes an upwardly extending finger 834 terminating at tip 838 and a downwardly extending finger 832 terminating at tip 836 for engaging a dental prosthesis.

In use, and as illustrated in FIGS. 9-13, the various dental tool embodiments, such as dental tools 320 and 720, are shown disengaging a dental appliance or prosthesis from a user's mouth. In FIG. 9, a dental appliance 26 is at least partially anchored in the user's mouth by a stainless steel wire 28 having a ball clasp 29 at an end thereof. Wire 28 is closely formed to the inner contour of the user's mandible 22 and extends upwardly and over the interstitial area between two adjacent teeth 24. Ball clasp 29 is firmly engaged in an undercut area of adjacent teeth 24. Since ball clasp is firmly engaged in the undercut area, it is difficult to disengage without the use of an instrument of one kind or another. By using dental tool 720, and more specifically upwardly extending finger 734, tip 738 can be inserted below ball clasp 29 by the user and urged upwardly around the contour of teeth 24 to disengage dental appliance 26 from the user's mouth.

As shown in FIG. 10, a user has a full maxillary denture 36 that fits to the user's maxillary arch 32. Maxillary arch 32 can also have one or more anchoring posts 34 that enhance the retention of denture 36. However, posts 34 also increase the force necessary to dislodge and remove denture 36. Dental tool 320 is used to aid in dislodging and removing denture 36 by engaging resilient tip 336 of downwardly extending finger 332 over a top edge 38 of denture 36 and then applying a downward force to handle 322 until denture 36 is dislodged from maxillary arch 32 and post 34. Denture 36 can then be grasped by the user and removed from the user's mouth.

Figure 11:
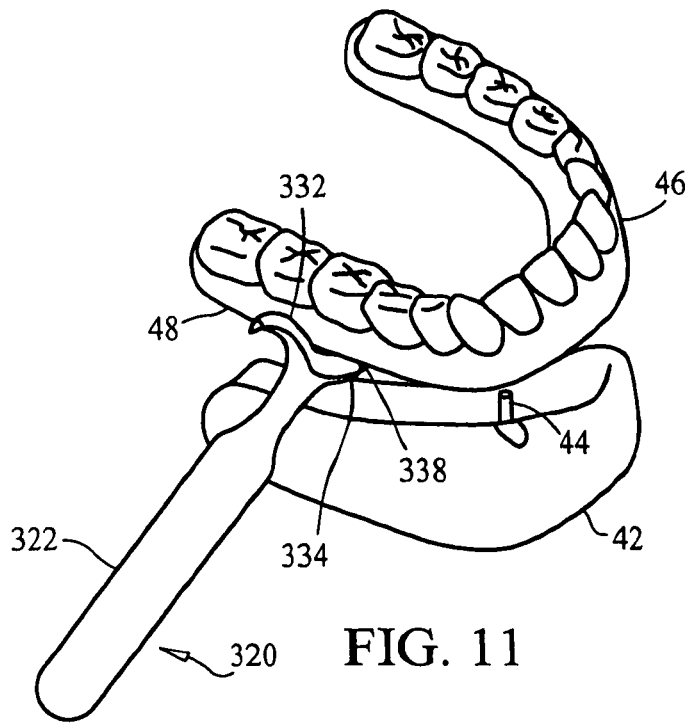
FIG. 11 is a perspective view of the dental tool as embodied by FIG. 3 dislodging a full mandibular denture from a user's mouth.

FIG. 11 illustrates the use of dental tool 320 in the dislodgment of a full mandibular denture 46 from a user's mandibular arch. The denture 46 can also be anchored in place by one or more anchoring posts 44. Resilient tip 338 of upwardly extending finger 334 is engaged under a lower edge 48 of denture 46 whereupon the user exerts an upward force to handle 322 until denture 46 is dislodged from mandibular arch 42 and anchoring posts 44. Denture 46 can then be grasped by the user and removed from the user's mouth.

Figure 12:
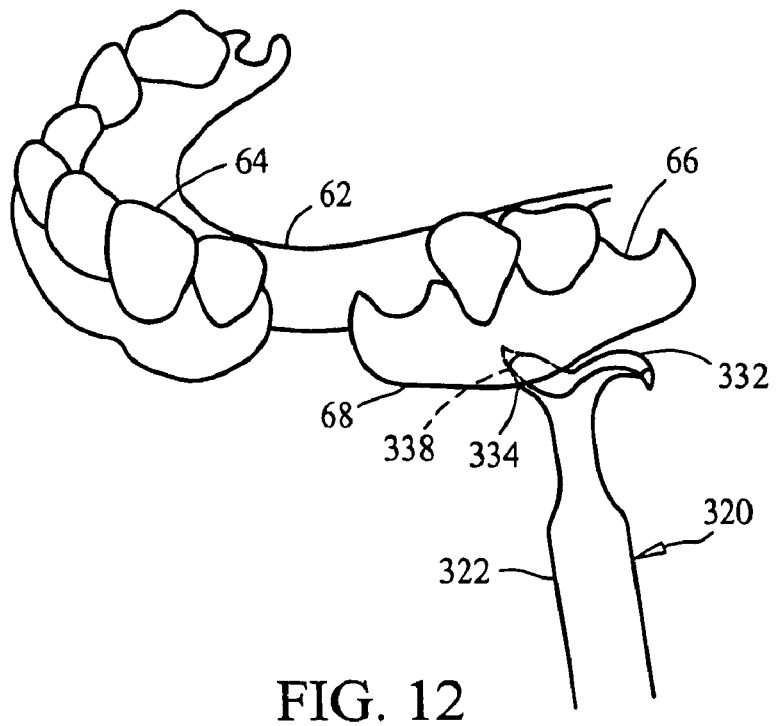
FIG. 12 is a perspective view of the dental tool as embodied by FIG. 3 dislodging a partial mandibular denture from a user's mouth.

As shown in FIG. 12, a user has a partial mandibular denture 66 that is retained in an area of the user's mandibular arch 62 that is missing a series of teeth 64. To remove the partial denture 66, tip 338 of upwardly extending finger 334 is placed under lower edge 68 of partial denture 66 whereupon the user exerts a gentle upward force to handle 322 until partial denture 66 is dislodged. Partial denture 66 can then be manually removed from the user's mouth.

Figure 13:
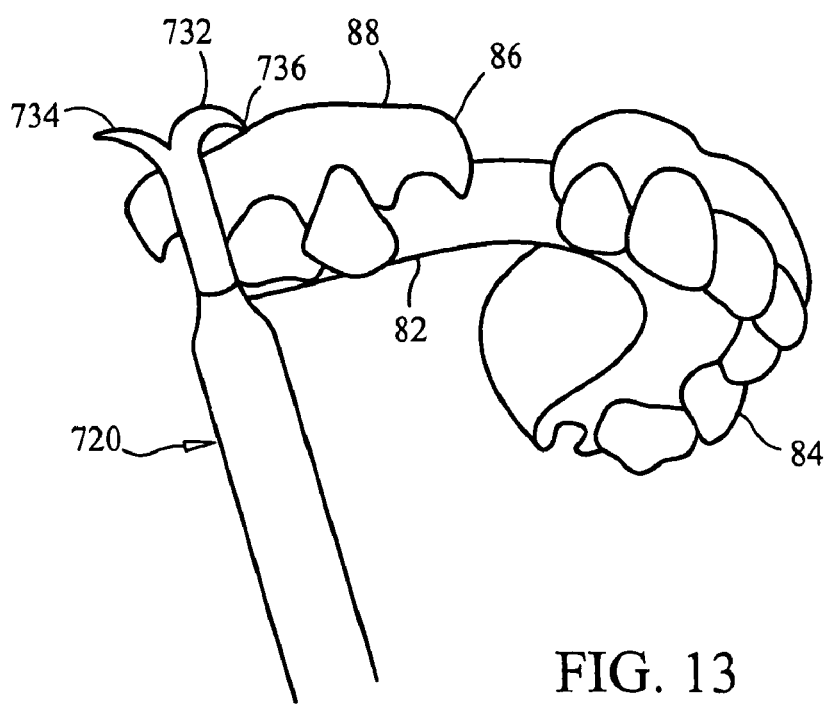
FIG. 13 is a perspective view of the dental tool as embodied by FIG. 7 dislodging a partial maxillary denture from a user's mouth.

Referring now to FIG. 13, a user has a partial maxillary denture 86 that replaces a series of missing teeth 84. To remove the partial denture 86 with dental tool 720, the tip 736 of downwardly extending finger 732 is engaged over a top edge 88 of partial denture 86 whereupon a downward force is applied to handle 722 until partial denture 86 is dislodged. Once partial denture 86 is dislodged, the denture 86 can then be removed from the user's mouth.

Figure 14:
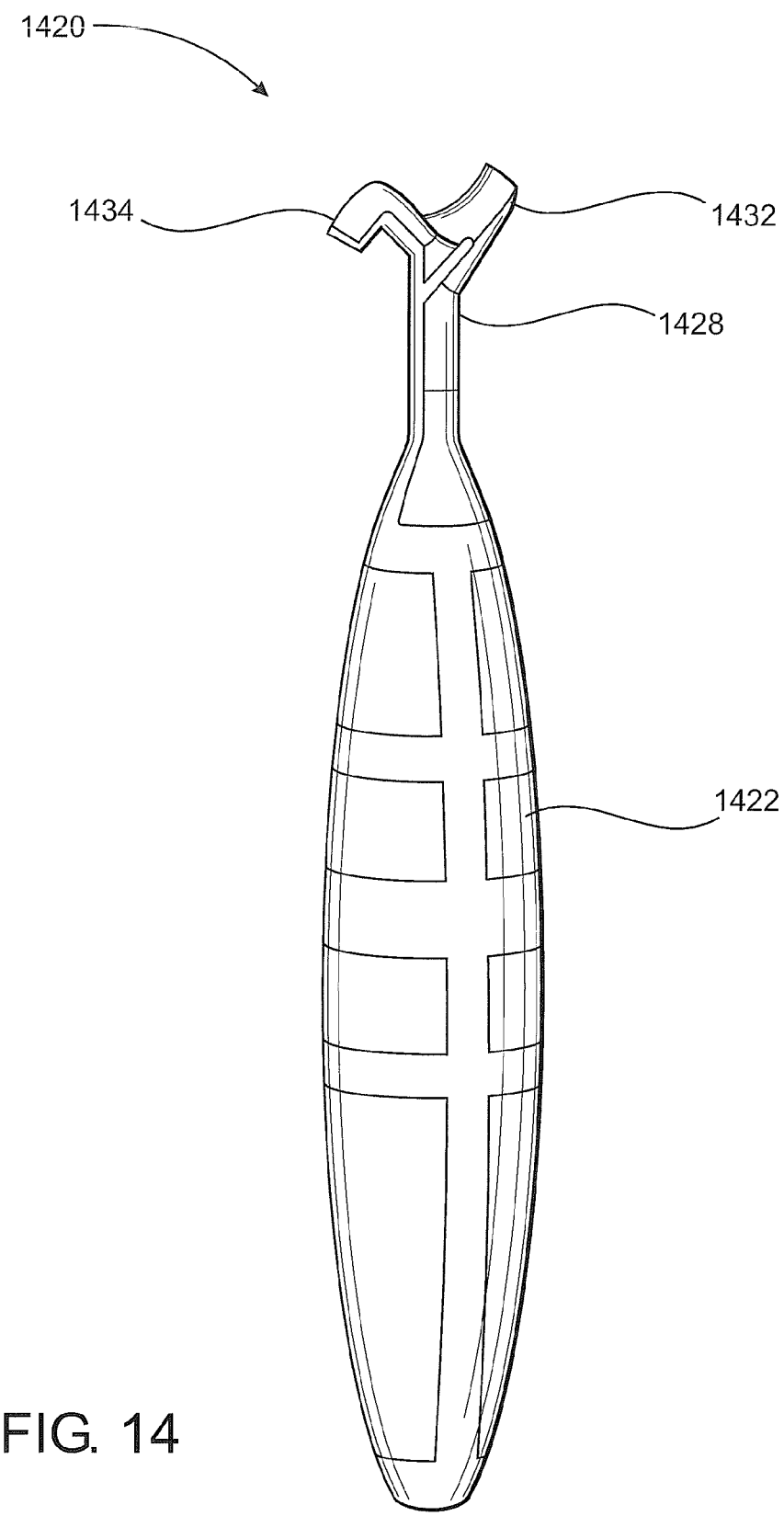
FIG. 14 is a perspective view of the dental tool embodying the present invention and having a universal handle, a first engagement member in angled relation to a second engagement member, and resilient material along at least a portion of the dental tool.

FIG. 14 depicts another embodiment of the present invention wherein dental tool 1420 comprises a universal handle 1422 which is configured to be symmetrical in all directions along its central longitudinal axis. This creates an omnidirectional grip of handle 1422 and allows a user to orient dental tool 1420 in a plurality of operative positions relative to the dental appliance or oral device to be removed from a user's mouth. It is also contemplated that universal handle 1422 is substantially cylindrical in shape, ergonomic, and shaped to fit comfortably in a user's hand while gripping and utilizing dental tool 1420.

Dental tool 1420 further comprises an engagement head 1428 having a first engagement member 1432 and a second engagement member 1434 extending therefrom and in opposite direction from handle 1422. First engagement member 1432 is structured to extend upward and outward in linear fashion from handle 1422 and terminates in a distal tip 1436. Second engagement member 1434 extends outward and substantially downward from engagement head 1428, terminating in distal tip 1438. It is contemplated that distal tips 1436 and 1438 have curvilinear edges, that is, broad and yet substantially rounded along their respective peripheries such that they imitate the shape of a fingernail, as depicted in FIG. 14B. This broad and curvilinear periphery allows for optimal contact and engagement between a distal tip 1436 or 1438 and a surface of a dental appliance or oral device to be removed.

Figure 14A:
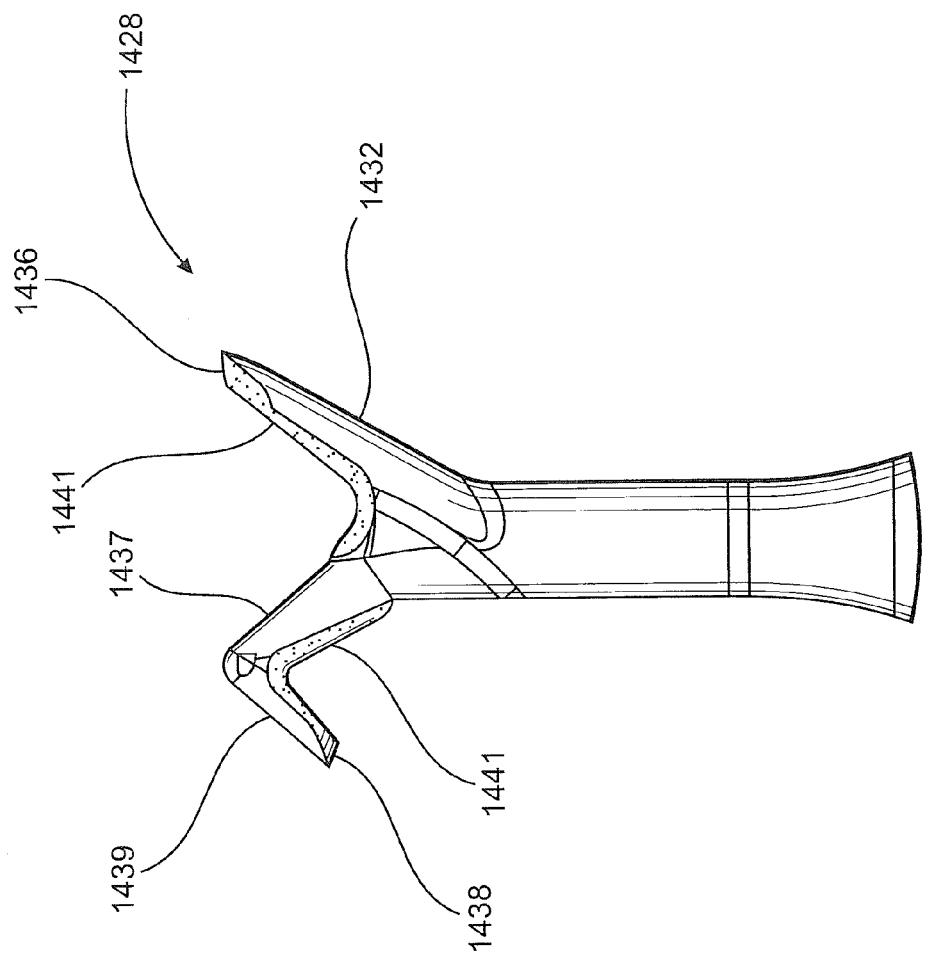
FIG. 14A is a side elevation view of the engagement head of the dental tool as embodied in FIG. 14 depicting the angled relation of the first and second engagement members.
Figure 14B:
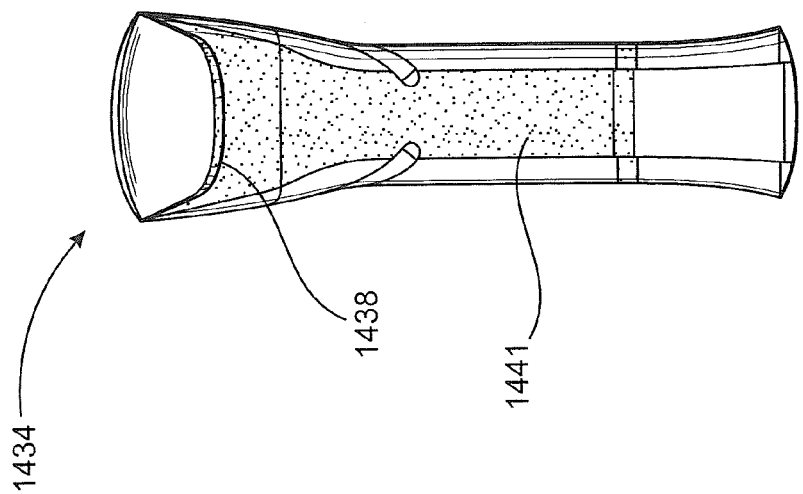
FIG. 14B is a front elevation view of the second engagement member as embodied in FIG. 14 depicting the distal tip and resilient material thereon.

FIG. 14A shows a side view of the engagement head 1428 of FIG. 14. The second engagement member 1434 is comprised of two portions; a primary portion 1437 which extends outward from handle 1422, and a secondary portion 1439 which extends downward from the end of primary portion 1437 opposite handle 1422. Primary portion 1437 and secondary portion 1439 are disposed in angled, rather than curved, relation to each other, enabling better contacting engagement of the dental appliance or oral device by the second engagement member 1434, not only at the distal tip 1438 but also along the surfaces of second engagement member 1434 which contact and engage the dental appliance or oral device. The first engagement member 1432 extends linearly in angled relation to the primary portion 1437 of the second engagement member 1434.

In one embodiment, and for illustrative purposes only, the first engagement member 1432 and the second engagement member 1434 are positioned at approximately a ninety (90) degree angle relative to each other. It is understood, however, that the present invention is not limited to this specific angle, and the first engagement member 1432 and second engagement member 1434 may in fact be angled at a variety of degrees, so long as they remain in angled relation to one another. The present invention does not consist of curved or ogee shaped engagement members, but rather angular engagement members. This achieves a more efficient contacting surface between the dental tool and the dental appliance or oral device to be removed.

To better assist in the removal of a dental appliance or oral device, the first engagement member 1432 and second engagement member 1434 of the present invention have surfaces along at least a portion of their length which will contact and/or engage the dental appliance or oral device to be removed. Specifically, the top surface of the first engagement member 1432 is structured to contact an oral device retained on the mandibular arch (lower jaw), whereas the bottom surface of the second engagement member 1434 is structured to contact an oral device retained on the maxillary arch (upper jaw). Once contact is made, gentle pressure is applied by the user of the dental tool 1420 in a direction opposite to that of the force retaining the dental appliance or oral device in place, until the dental appliance or oral device is free of the mucosa, teeth, or other support within the mouth and may be removed. The dental tool 1420 of the present invention is therefore necessarily comprised of a rigid material such that it can withstand the forces of removal while retaining its shape so as to be effective. By way of example only, the dental tool 1420 may be comprised of hard plastic, though it is understood that it may be made of any rigid material which would allow it to retain its shape under gentle to moderate pressure.

In order to prevent damage to the teeth or underlying mucosa of the mouth during contact and removal of a dental appliance or oral device, the contact surfaces of the first engagement member 1432 and second engagement member 1434 are covered or overlaid with a resilient material or portion 1441 which serves to cushion the contact. For instance, the resilient portion 1441 may be rubber. It is understood, however, that the resilient portion 1441 may be made of any material which is softer than the remainder of the dental tool 1420, can absorb shock or pressure and then rebound to its original shape once the pressure has subsided, and is at least thick/dense enough to effectively buffer the dental appliance or oral device from the more rigid underlying material of the dental tool 1420. This resilient portion 1441 prevents the dental appliance or oral device from being scratched or otherwise damaged by the dental tool 1420 during removal.

It is also contemplated, as depicted in FIGS. 14A and 14B, that the distal tips 1436 and 1438 of the first engagement member 1432 and second engagement member 1434, respectively, are also at least partially overlaid with a resilient portion 1441 to protect the teeth and mucosa of the mouth from being cut, scratched, torn, or otherwise irritated or damaged during the contact of the dental tool 1420 with the dental appliance or oral device and removal of the same. This decrease in potential tissue damage also reduces the risk of infection, as it prevents the tissue of the mouth from being compromised and open to bacteria and other infectious microbes. As is clear from the drawings, the resilient portion 1441 may overlay at least the peripheral portion of the distal tips 1436 and 1438 which makes contact with the dental appliance or oral device. However, it is also contemplated that the distal tips 1436 and 1438 may be entirely covered in the resilient portion 1441 (not shown).

Figure 15:
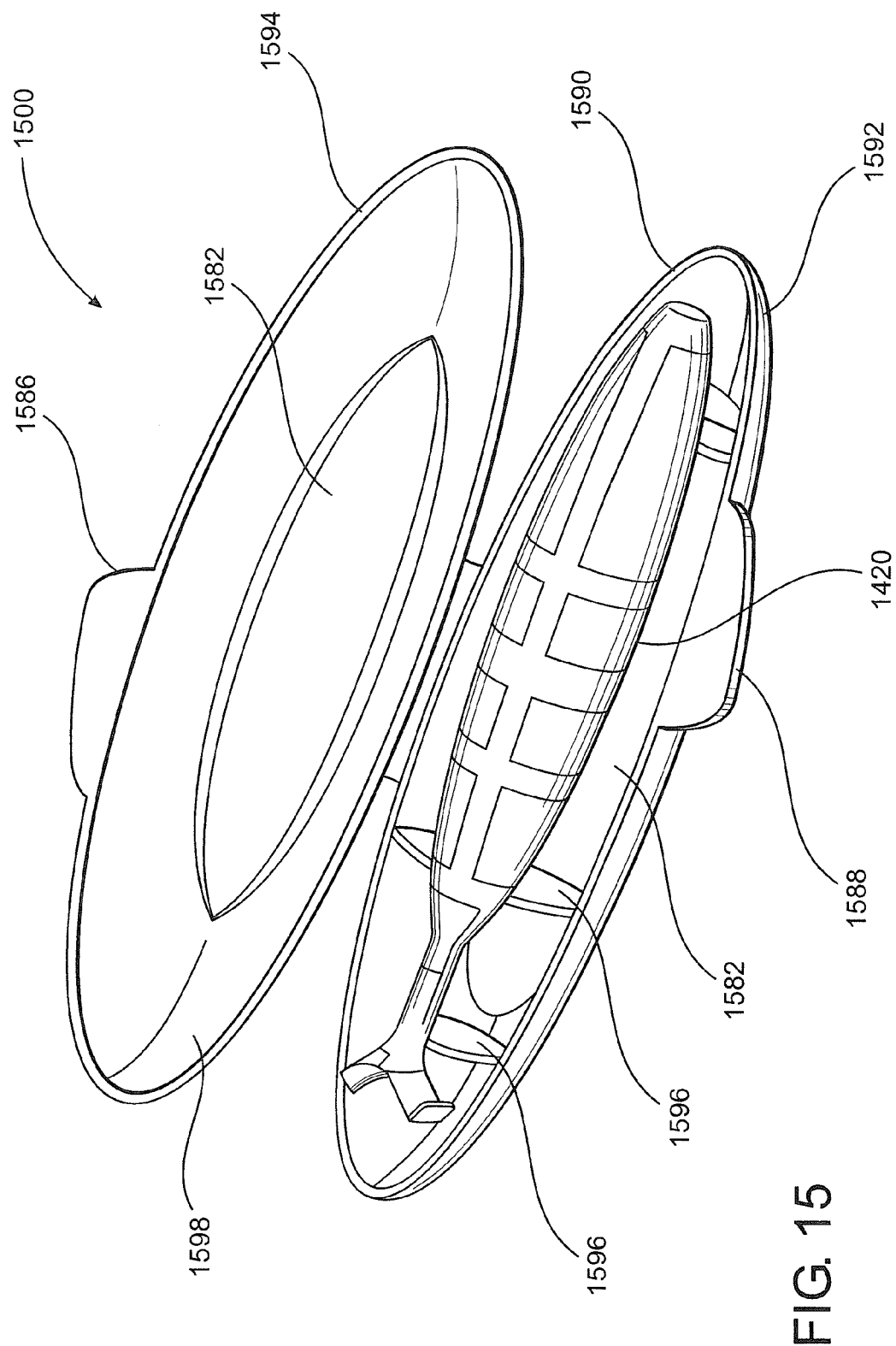
FIG. 15 is a perspective view of a kit for removal of an oral device.

FIG. 15 shows another aspect of the present invention, which is a kit 1500 for removing an oral device. This kit comprises a dental tool 1420 and a case 1590 having a bottom 1592 and top 1594 such that case 1590 is disposed between an open configuration and a closed configuration. In one embodiment, the bottom 1592 and top 1594 may be interconnected, such as by a hinge, so that the case 1590 can open and close about the hinge. However, other methods of opening and closing the case 1590 are contemplated herein. Case 1590 is further structured to create an inner cavity 1598, which is structured to accommodate dental tool 1420 therein in either the open or closed configuration, or any intermediate configuration there between. In at least one embodiment, at least a portion of bottom 1592 comprises a planar surface 1582. Similarly, at least a portion of top 1594 may also comprise a planar surface 1582. It can be appreciated that planar surface 1582 is structured and disposed to enhance the stability of case 1590 while still allowing sufficient space in the inner cavity 1598 to fully accommodate dental tool 1420 within case 1590, even when case 1590 is in the closed configuration.

Bottom 1592 and top 1594 are cooperatively structured to matingly engage each other in the closed configuration, and yet are releasable to allow for movement between closed and open configurations. In one embodiment, bottom 1592 comprises a first fastening member 1586, and correspondingly, top 1594 comprises a second fastening member 1588. Accordingly, first fastening member 1586 and second fastening member 1588 are structured and disposed to interact with one another to facilitate the releaseable engagement of bottom 1592 and top 1594 in order to achieve a fully closed configuration of case 1590. For example, first fastening member 1586 and second fastening member 1588 may be structured as tabs, and may be interlocking, although other structures are also contemplated.

Case 1590 further comprises a plurality of support members 1596 which are affixed to the inside of bottom 1592, and are structured and disposed to receive dental tool 1420 and support it within case 1590. The kit 1500 thus provides for easy and hygienic storage and portability of dental tool 1420.

The above description is considered that of the illustrated embodiments only. Modifications of the invention will occur to those skilled in the art and to those who make or use the invention. Therefore, it is understood that the embodiments shown in the drawings and described above are merely for illustrative purposes and are not intended to limit the scope of the invention, which is defined by the following claims as interpreted according to the principles of patent law, including the doctrine of equivalents.

What is claimed is:

1. A dental tool for removing an oral device from a user's mouth comprising:
   a handle,
   an engagement head interconnected to said handle, said engagement head comprising a first engagement member and a second engagement member,
   said first engagement member comprises a substantially linear configuration and is structured and configured to extend upwardly and outwardly relative to said handle,
   said second engagement member comprises a primary portion and a secondary portion, wherein said primary portion is structured and configured to extend upwardly and outwardly relative to said handle and said secondary portion is structured and configured to extend downwardly and outwardly relative to said first engagement member, and said primary portion and said secondary portion of said second engagement member are disposed in an angled relation to one another, and are structured and configured to form a substantially ninety degree angle therebetween,
   said first engagement member extends linearly in an angled relation to said primary portion of said second engagement member,
   at least a portion of each of said first engagement member and said second engagement member comprising a resilient portion disposed in overlying relation thereto, and
   each of said first engagement member and said second engagement member comprising a distal tip having a substantially curvilinear peripheral edge.

2. A dental tool as recited in claim 1 wherein said handle comprises a substantially cylindrical shape.

3. A dental tool for removing an oral device from a user's mouth comprising:
   a handle comprising a substantially cylindrical shape,
   an engagement head interconnected to said handle,
   said engagement head comprising a first engagement member structured and configured to extend upwardly and outwardly relative to said handle, wherein said first engagement member comprises a substantially linear configuration,
   said first engagement member comprising a contact surface disposed to engage the oral device,
   said engagement head further comprising a second engagement member structured and configured to extend outwardly relative to said handle, said second engagement member comprising a contact surface disposed to engage the oral device, said second engagement member comprises a primary portion structured and configured to extend upwardly and outwardly from said handle and a secondary portion structured and configured to extend downwardly and outwardly relative to said first engagement member, and said primary portion and said secondary portion of said second engagement member are structured and configured to form a substantially ninety degree angle therebetween, said handle and said engagement head constructed of a substantially rigid material, said engagement head comprising a resilient portion, said resilient portion disposed in overlying relation to at least a portion of said contact surface of said first engagement member, and said resilient portion further disposed in overlying relation to at least a portion of said contact surface of said second engagement member.

4. A dental tool as recited in claim 3 wherein said first engagement member is disposed in an angled relation to said primary portion of said second engagement member.

5. A dental tool as recited in claim 4 wherein said first engagement member and said primary portion of said second engagement member form at least a ninety degree angle therebetween.

* * * * *